(12) United States Patent
Nakama

(10) Patent No.: US 7,280,213 B2
(45) Date of Patent: Oct. 9, 2007

(54) LIGHT DETECTION DEVICE

(75) Inventor: Kenichi Nakama, Tokyo (JP)

(73) Assignee: Nippon Sheet Glass Company, Limited (JP)

( * ) Notice: Subject to any disclaimer, the term of this patent is extended or adjusted under 35 U.S.C. 154(b) by 365 days.

(21) Appl. No.: 11/130,491

(22) Filed: May 17, 2005

(65) Prior Publication Data

US 2005/0259258 A1 Nov. 24, 2005

(30) Foreign Application Priority Data

May 19, 2004 (JP) ............. 2004-149528

(51) Int. Cl.
- G01N 21/25 (2006.01)
- G01J 3/30 (2006.01)
- G01B 11/24 (2006.01)
- G01B 11/30 (2006.01)

(52) U.S. Cl. .............. 356/417; 356/317; 356/378; 356/612

(58) Field of Classification Search ........ 356/337–343, 356/402–425, 445–448, 256, 317–318; 250/216–227.32, 250/234–236, 458.1, 459.1; 422/52, 65

See application file for complete search history.

(56) References Cited

U.S. PATENT DOCUMENTS

| 4,580,895 A * | 4/1986 | Patel ............. 356/39 |
| 6,373,573 B1 * | 4/2002 | Jung et al. ............. 356/419 |
| 6,800,844 B2 * | 10/2004 | Kandori et al. ............. 250/234 |
| 6,891,620 B2 * | 5/2005 | Mukai et al. ............. 356/445 |
| 2003/0189707 A1 * | 10/2003 | Naya et al. ............. 356/445 |

FOREIGN PATENT DOCUMENTS

JP  2000-249650  9/2000

\* cited by examiner

Primary Examiner—Gregory J. Toatley, Jr.
Assistant Examiner—Jarreas Underwood
(74) Attorney, Agent, or Firm—Caesar, Rivise, Bernstein, Cohen & Pokotilow, Ltd.

(57) ABSTRACT

A microplate reader includes a light emitting portion for irradiating each of a plurality of test samples with excitation light, a light receiving portion for receiving return light from each of the test samples, and an XY stage for moving the light emitting portion and the light receiving portion to traverse and scan the test samples. The light emitting portion and the light receiving portion are defined at the same location on a reflection surface, which is formed on a distal end of a glass light guide rod. The light emitting portion irradiates each test sample with a sufficient amount of excitation light so that a sufficient amount of return light enters the light receiving portion.

14 Claims, 4 Drawing Sheets

LIGHT DETECTION DEVICE

CROSS-REFERENCE TO RELATED APPLICATIONS

This application is based upon and claims the benefit of priority from prior Japanese Patent Application No. 2004-149528, filed on May 19, 2004, the entire contents of which are incorporated herein by reference.

BACKGROUND OF THE INVENTION

The present invention relates to a light detection device for detecting return light from a test sample that is irradiated with excitation light.

A conventional light detection device irradiates test samples with excitation light and detects return light (luminescence, fluorescence, reflected light, or scattered light) from the test samples to analyze the test samples based on the return light.

Conventionally, test samples are accommodated in wells formed on a microplate. A conventional light detection device, such as a fluorescent microscope or a microplate reader, entirely irradiates the microplate with excitation light having a specific wavelength to generate an image of the entire surface of the microplate, that is, to generate an image of all the test samples, based on return light, with an imaging device, such as a charge-coupled device (CCD) camera. The resulting image data is then subjected to image processing to analyze each test sample.

A conventional light detection device is designed for use in, for example, a large laboratory. The light detection device irradiates the entire surface of the microplate with excitation light. In this case, parts of the microplate surface on which the test samples are not arranged are also irradiated with excitation light. Thus, the density of excitation light received by each test sample is low. As a result, return light from each test sample is weak. Accordingly, the detection sensitivity of the light detection device is low.

Japanese Laid-Open Patent Publication No. 2000-249650 describes an improvement of such a microplate reader. The improved microplate reader includes a plurality of light guides and a plurality of light receiving portions arranged for a plurality of test samples, respectively. Excitation light from a single light source is guided through the light guides to irradiate the test samples. Thus, only the parts of the microplate surface on which the test samples are arranged are irradiated with excitation light.

However, the microplate reader is not preferable for use when it includes a compact microplate on which a large number of wells are densely arranged.

(1) Normally, a large number of wells are densely arranged on a compact microplate in a matrix-like manner. A large number of light guides, each associated with one of the densely arranged wells, occupy a large capacity and enlarges the microplate reader. This structure fails to provide a portable microplate reader. Further, this structure requires the difficult task of arranging the large number of light guides on the microplate.

(2) With this structure, excitation light from the single light source is split and provided to the plurality of test samples via the large number of light guides. The amount of excitation light per light guide is small. Thus, the return light from each test sample is weak. Accordingly, the detection sensitivity of this microplate reader is low.

(3) With this structure, the light receiving portions are arranged two-dimensionally. Thus, each light receiving portion may receive leakage light from adjacent light receiving portions. Such leakage light lowers the detection accuracy of return light, which in turn, lowers the analysis accuracy of the test samples.

SUMMARY OF THE INVENTION

It is an object of the present invention to provide a compact light detection device having high detection sensitivity at a low cost.

One aspect of the present invention is a light detection device for irradiating each of a plurality of test samples, respectively accommodated in a plurality of measurement areas, with excitation light, and detecting return light from each of the test samples. Each measurement area has a predetermined dimension. The light detection device includes a light emitting portion for irradiating each measurement area with the excitation light. A light receiving portion, spaced from the light emitting portion by a predetermined distance, receives the return light. The predetermined distance is less than the predetermined dimension. A scanner moves the light emitting portion and the light receiving portion in a range including the plurality of measurement areas and scanning the measurement areas.

Another aspect of the present invention is a light detection device for emitting excitation light beam to one of a plurality of test samples placed on a substrate, and detecting return light beam from the one of the test samples. Each sample has a diameter. The light detection device includes a set of a light emitting portion for irradiating one of the test samples with the excitation light beam and a light receiving portion for receiving the return light beam. The light receiving portion is spaced from the light emitting portion by a predetermined distance that is less than the diameter of each test sample. A scanner moves said set of the light emitting portion and the light receiving portion within a stroke so as to traverse the test samples to scan the test samples.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

A light detection device according to a first embodiment of the present invention will now be described.

Figure 1:
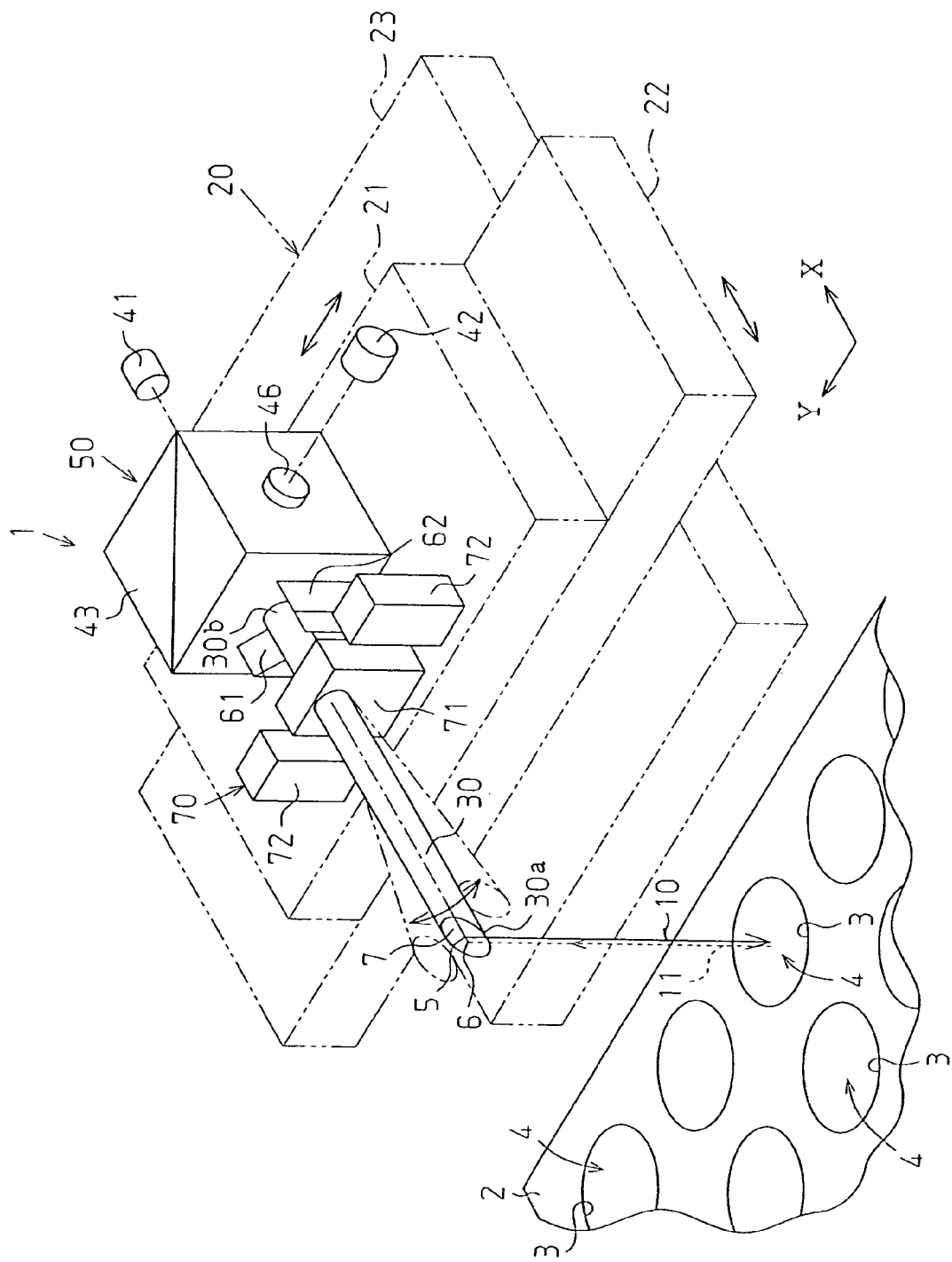
FIG. 1 is a perspective view showing a microplate reader according to a first embodiment of the present invention.

Referring to FIG. 1, a microplate reader 1, which functions as a light detection device, emits excitation light to illuminate one of a plurality of test samples 4 and receives return light from the test sample to analyze the test sample. The test samples 4 are respectively accommodated in a plurality of measurement areas. The test sample is analyzed qualitatively or quantitatively based on the return light.

A plurality of wells 3 are two-dimensionally arranged, that is, arranged in a matrix manner, on a microplate 2 or a microarray, which functions as a substrate. The test samples 4 are each accommodated in one of the wells 3 on the microplate 2. In this case, each well 3 defines the measurement area of its accommodating test sample 4. The test samples 4 may be placed on the microplate 2. In this case, upper surface of each test sample 4 defines the measurement area of its test sample 4.

As shown in FIGS. 1 and 2, the microplate reader 1 includes a light emitting portion 5 and a light receiving portion 6. The light emitting portion 5 illuminates a test sample 4 with excitation light 10. The light receiving portion 6 receives return light 11 from the test sample 4. The return light 11 includes, for example, luminescence, fluorescence, reflected light, or scattered light from the test sample. Hereafter, the microplate reader 1 detects fluorescence included in the return light 11. The light emitting portion 5 and the light receiving portion 6 are arranged close to each other. In detail, the distance between the light emitting portion 5 and the light receiving portion 6 is substantially equal to or less than the diameter of each well 3 (the dimension at the top surface of each test sample 4). The microplate reader 1 includes an XY stage 20 for moving the light emitting portion 5 and the light receiving portion 6 to sequentially scan the test samples 4. A scanner including the XY stage 20 moves the light emitting portion 5 and the light receiving portion 6 sequentially to the wells 3 on the microplate 2.

Figure 2A:
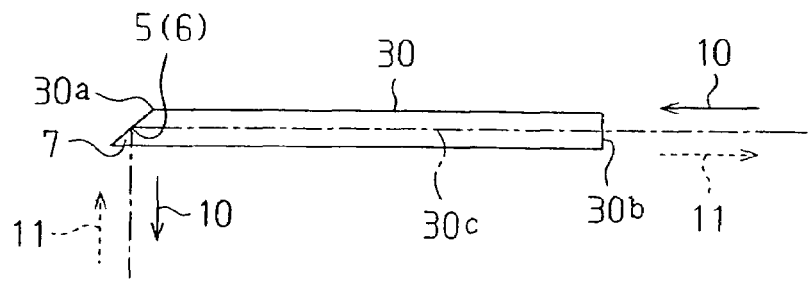
FIG. 2A is a side view showing a glass light guide rod.
Figure 2B:
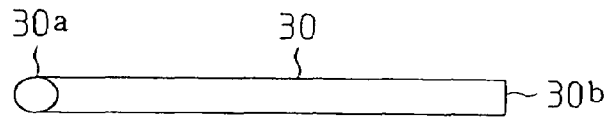
FIG. 2B is a plan view showing the light guide rod.

In the first embodiment, the light emitting portion 5 and the light receiving portion 6 are formed as parts of a reflection surface 7. The reflection surface 7 is formed on a distal end 30a of a single light guide rod 30. The light guide rod 30 is made of glass and formed by, for example, an optical fiber including a core and a cladding. As shown in FIGS. 2A and 2B, the reflection surface 7 is an inclined surface formed by polishing the distal end 30a of the light guide rod 30. The reflection surface 7 is inclined at an angle of 45 degrees with respect to the core axis 30c. As shown in FIG. 2A, the light emitting portion 5 and the light receiving portion 6 may be defined at the same position on the reflection surface 7 of the light guide rod 30.

Figure 3:
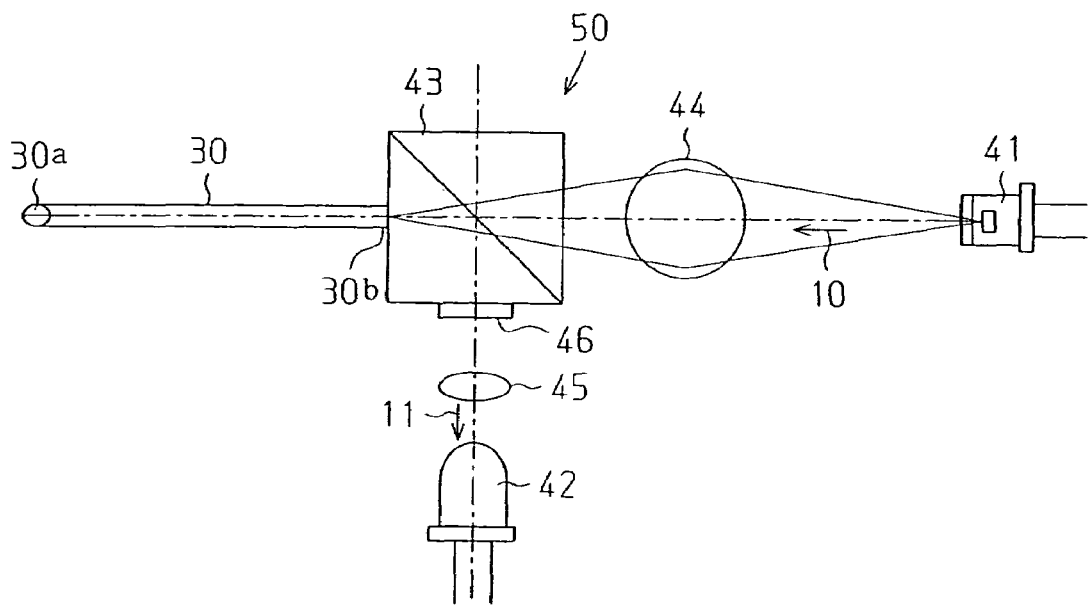
FIG. 3 is a plan view showing an optical system.

As shown in FIGS. 1 and 3, the microplate reader 1 includes a light source 41, a photodetector 42, and an optical system 50. The light source 41 emits the excitation light 10. The photodetector 42 detects the fluorescence 11. The optical system 50 is optically coupled to the light source 41 and the photodetector 42. The optical system 50 directs the excitation light 10 from the light source 41 to enter the basal end 30b of the light guide rod 30. Further, the optical system 50 directs the fluorescence 11 from the basal end 30b to enter the photodetector 42. In the first embodiment, the excitation light 10 is a laser beam having a specific wavelength.

As shown in FIG. 3, the optical system 50 includes a spherical lens 44, a wavelength division multiplexing element (beam splitter) 43 functioning as a wavelength division element, a converging lens 45, and a filter 46. The spherical lens 44 directs the excitation light 10 from the light source 41 to pass through the beam splitter 43 and converge at the basal end 30b of the light guide rod 30. The beam splitter 43 permits passage of the excitation light 10. Further, from the light that returns via the basal end 30b of the light guide rod 30, the beam splitter 43 selectively reflects only light (fluorescence 11) having a wavelength differing from the wavelength of the excitation light 10. The converging lens 45 focuses the reflected fluorescence 11 on the photodetector 42. The filter 46 cuts out the excitation light 10 to prevent the excitation light 10 from entering the photodetector 42. The spherical lens 44 and the converging lens 45 are not shown in FIG. 1.

The beam splitter 43 is fixed to a movable table 21 on the XY stage 20. A holding member (not shown), which is fixed to the movable table 21, holds the components of the optical system 50 except for the beam splitter 43.

Figure 4:
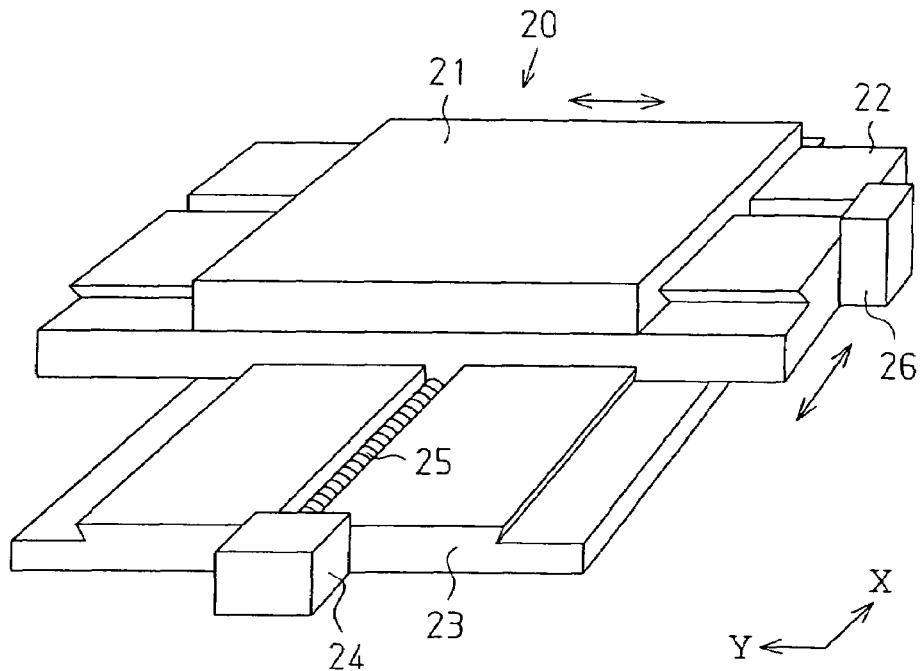
FIG. 4 is a perspective view showing an XY stage.

As shown in FIG. 4, the XY stage 20 includes the movable table 21, a Y-drive table 22, and an X-drive table 23. The Y-drive table 22 supports the movable table 21 in a manner movable in the Y-axis direction. The X-drive table 23 supports the Y-drive table 22 in a manner movable in the X-axis direction. The X-drive table 23 includes an X-motor 24 and a screw shaft 25 extending in the X-axis direction. The X-motor 24 rotates the screw shaft 25 to move the Y-drive table 22 and the movable table 21 in the X-axis direction. The Y-drive table 22 includes a Y-motor 26 and a screw shaft (now shown) extending in the Y-axis direction. The Y-motor 26 rotates the screw shaft to move the movable table 21 in the Y-axis direction. The movement of the movable table 21 moves the light emitting portion 5 and the light receiving portion 6 along an XY plane.

Figure 5:
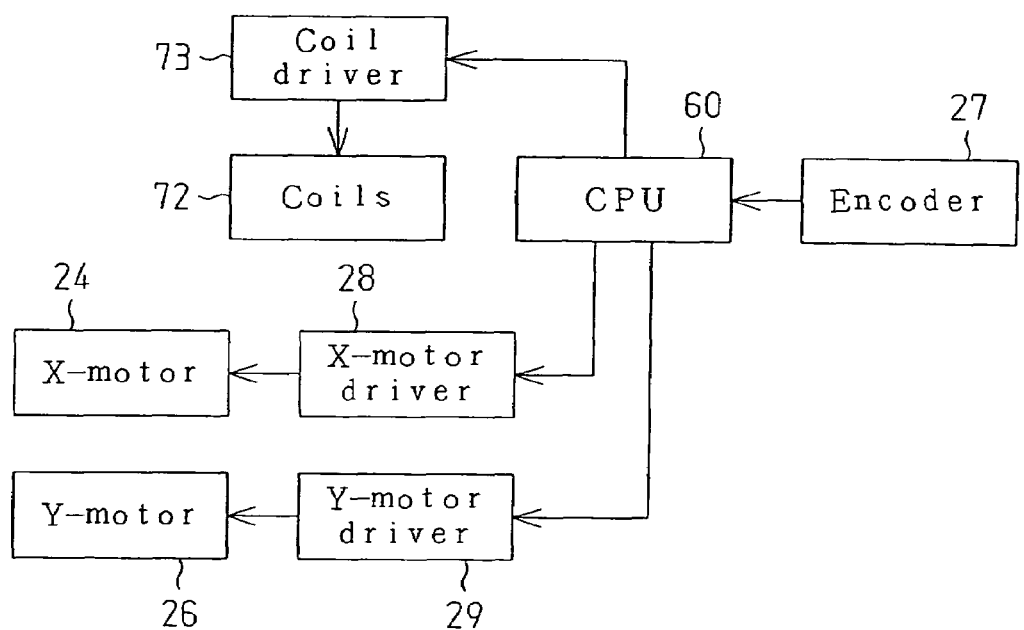
FIG. 5 is a block diagram showing the electric configuration of the microplate reader.

The scanner further includes an encoder 27, an X-motor driver 28, a Y-motor driver 29, and a CPU 60 (refer to FIG. 5). The encoder 27 detects the position (X and Y coordinates) of the movable table 21. The CPU 60 is connected to the encoder 27 and the motor drivers 28 and 29. The CPU 60 generates a motor control signal in accordance with a position signal indicating the position of the movable table 21, which is detected by the encoder 27, and provides the motor drivers 28 and 29 with the motor control signal. The motor drivers 28 and 29 drive the X-motor 24 and the Y-motor 26 in accordance with the motor control signal. For example, the CPU 60 drives the X-motor 24 and the Y-motor 26 so that the light emitting portion 5 and the light receiving portion 6 sequentially scan the matrix of the test samples 4 on the microplate 2 from the first column of the first row to the last column of the last row.

As shown in FIG. 1, two supporting members 61 and 62 are fixed to the movable table 21. The supporting members 61 and 62 hold the basal end 30b of the light guide rod 30. The light guide rod 30, which is supported in a cantilevered manner, may be vibrated about the basal end 30b.

The microplate reader 1 includes a vibration unit 70. The vibration unit 70 uses electromagnetic force to vibrate the light guide rod 30 in the Y-axis direction (in one direction) along the XY plane, which is parallel to the microplate 2. The vibration unit 70 includes a permanent magnet 71, a pair of magnet coils 72, and a coil driver 73 (refer to FIG. 5). The permanent magnet 71 is arranged on the light guide rod 30 at a position close to the basal end 30b. The magnet coils 72 are arranged to sandwich the permanent magnet 71 and are fixed to the movable table 21. The coil driver 73 supplies the magnet coils 72 with excitation current.

Figure 6:
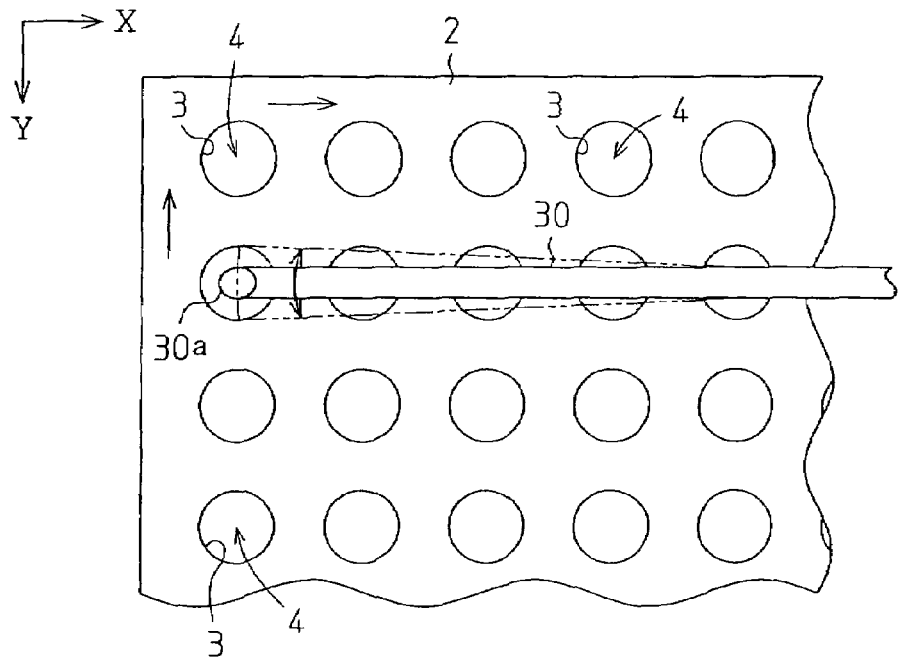
FIG. 6 is a diagram showing a scanning operation of the microplate reader.

The CPU 60 changes the direction of the exciting current flowing through the magnet coils 72 to change the magnetic pole of the surfaces facing the magnet coils 72 of the permanent magnet 71. The light guide rod 30 vibrates, or swings back and forth, about the basal end 30b in the Y-axis direction within the range indicated by a broken line in FIG. 6. It is preferred that the vibration width of the distal end 30a of the light guide rod 30 be substantially equal to the dimension of the top surface of each test sample 4, that is, the diameter of each well 3.

The spherical lens 44 converges the excitation light 10 at the basal end 30b of the light guide rod 30. The excitation light 10 travels toward the distal end 30a of the light guide rod 30 and is reflected by the light emitting portion 5 on the reflection surface 7. The reflected excitation light 10 travels downward in a direction perpendicular to the core axis 30c of the light guide rod 30 and enters one of the test samples 4 (refer to FIG. 1).

The test sample 4 illuminated with the excitation light 10 emits fluorescence 11. The fluorescence 11 is reflected by the light receiving portion 6 on the reflection surface 7 of the light guide rod 30 and guided into the light guide rod 30 so that it travels toward the basal end 30b of the light guide rod 30. The fluorescence 11 emitted from the basal end 30b is reflected by the beam splitter 43 so that it passes through the filter 46. Then, the fluorescence 11 is converged by the converging lens 45 so that it enters the photodetector 42. The photodetector 42 detects the intensity and/or wavelength of the incident fluorescence 11 and generates a detection signal in accordance with the intensity and/or the wavelength. A computer (not shown) qualitatively and/or quantitatively analyzes the test sample in accordance with the detection signal.

The scanner mechanically moves the light guide rod 30. The light emitting portion 5 and the light receiving portion 6 scan the matrix of the test samples 4, which are arranged on the microplate 2 in a two-dimensional manner, sequentially from the test sample 4 in the first column of the first row of the matrix to the test sample 4 in the last column of the last row of the matrix. This generates a detection signal that is in accordance with the intensity and/or the wavelength of the fluorescence 11 emitted from each test sample 4. Each detection signal is stored in association with the corresponding position of the movable table 21 and analyzed. Each test sample is analyzed qualitatively or quantitatively in accordance with the corresponding detection signal.

Relationship Between Fluorescent Dye and Excitation Light

The test sample 4 is a biological sample, such as DNA, dyed with, for example, a fluorescent dye. To analyze the test sample 4 when dyed with a fluorescent dye Cy3, a YAG laser device that oscillates the excitation light 10 having a wavelength of 532 nm may be used as the light source 41. In this case, return light from the test sample 4 includes the fluorescence 11 having a wavelength of 570 nm.

To analyze the test sample 4 when dyed with a fluorescent dye Cy5, a helium neon (HeNe) laser device that oscillates the excitation light 10 having a wavelength of 633 nm may be used as the light source 41. In this case, return light from the test sample 4 includes the fluorescence 11 having a wavelength of 670 nm.

The first embodiment has the advantages described below.

The microplate reader 1 includes the single light emitting portion 5 and the single light receiving portion 6, which are spaced from each other by a distance that is equal to or less than the dimension of the top surface of each test sample 4. The scanner moves the single light emitting portion 5 and the single light receiving portion 6 to sequentially scan the plurality of test samples 4. The light emitting portion 5 irradiates each test sample 4 with the excitation light 10. The light receiving portion 6 receives the fluorescence 11 from each test sample 4. This irradiates the small test samples 4, which are densely arranged, with a sufficient amount of excitation light 10. Thus, the intensity of return light from each test sample 4 is high. Accordingly, the detection sensitivity of the microplate reader 1 of the first embodiment is high.

One set of the light emitting portion 5 and the light receiving portion 6 is provided for the densely arranged plurality of small test samples 4. This structure eliminates the need for a large number of light guides as in the prior art example described above. Thus, the microplate reader 1 of the first embodiment is compact and inexpensive.

The light emitting portion 5 and the light receiving portion 6 are defined on parts of the reflection surface 7, which is formed on the distal end 30a of the glass light guide rod 30. This eliminates the need for additionally arranging a light source and a photodetector on the distal end 30a of the light guide rod 30 and the need for arranging electric wirings on the light guide rod 30. Thus, the microplate reader 1 of the first embodiment has high reliability and long durability.

The set of the light emitting portion 5 and the light receiving portion 6 scans the plurality of test samples 4. The light emitting portion 5 and the light receiving portion 6 are located at the same position on the distal end 30a of the single light guide rod 30. The light emitting portion 5 and the light receiving portion 6 are obtained when polishing the distal end 30a of the single light guide rod 30 to form the reflection surface 7. This eliminates the need for arranging more light guide rods 30 or changing the structure of the light guide rod 30 even when increasing the quantity of the test samples 4 that are to be analyzed. The same light guide rod 30 may be used regardless of the shape of the microplate 2 or the arrangement of the wells 3. Thus, the microplate reader 1 of the first embodiment is highly versatile and inexpensive.

The excitation light 10 is guided from the light source 41 into the light guide rod 30 and supplied from the light emitting portion 5 to each test sample 4. The fluorescence 11 from each test sample 4 is guided into the light guide rod 30 by the light receiving portion 6, travels through the light guide rod 30 in the direction opposite to the traveling direction of the excitation light 10, and enters the photodetector 42. Loss in the excitation light 10 and the fluorescence 11 is small, and the detection accuracy of the fluorescence 11 from each test sample 4 is high.

The beam splitter 43 permits passage of the excitation light 10 from the light source 41. Further, from the light that returns via the basal end 30b of the light guide rod 30, the beam splitter 43 reflects only return light (i.e., fluorescence) having a wavelength that differs from the wavelength of the excitation light 10. The excitation light 10 and the fluorescence 11, which have different wavelengths, use the same optical system 50. Accordingly, the microplate reader 1, which includes the optical system 50 having a simple structure, is inexpensive.

The scanner including the XY stage 20, the encoder 27, the CPU 60, and the motor drivers 28 and 29 mechanically moves the light emitting portion 5 and the light receiving portion 6 in a one-dimensional or two-dimensional manner with respect to the microplate 2, which is held in a fixed state. In this way, the light emitting portion 5 and the light receiving portion 6 scan the plurality of test samples 4. The scanner mechanically moves the single light emitting portion 5 and the single light receiving portion 6 in a two-dimensional manner to scan the plurality of test samples 4. This provides each of the plurality of test samples 4 with the excitation light 10 and detects the fluorescence 11 from each test sample 4. Thus, the microplate reader 1 is compact, inexpensive, and highly versatile.

The XY stage 20 of the scanner moves the movable table 21 in the X direction and in the Y direction along the XY plane that includes the test samples 4. The basal end 30b of the light guide rod 30 moves integrally with the movable table 21. Thus, the light guide rod 30 moves in the X direction and in the Y direction along the XY plane including the test samples 4. The XY stage 20 moves the single light emitting portion 5 and the single light receiving portion 6 in a two-dimensional manner to scan the test samples 4.

The basal end 30b of the light guide rod 30 is supported in a cantilevered manner so that the light guide rod 30 swings about its basal end 30b. The vibration unit 70 uses electromagnetic force to vibrate the distal end 30a of the light guide rod 30 parallel to the Y-axis on the XY plane. The scanner mechanically moves the single light emitting portion 5 and the single light receiving portion 6 in a two-dimensional manner while vibrating the vibration unit 70 to sequentially scan the plurality of test samples 4. The positioning of the light guide rod 30 with respect to the test samples 4 performed before starting measurement does not require high accuracy. This facilitates measurement preparations.

The light guide rod 30 is made of glass, which is less likely to break due to fatigue than metal when subjected to vibrations. The light guide rod 30 has high durability and requires less maintenance work. Thus, the microplate reader 1 has high reliability and long durability.

The glass light guide rod 30, which is vibrated, includes components such as a photodetector, a light emitting element, and electric wirings. This facilitates the assembly of the microplate reader 1. The microplate reader 1 is easily assembled and suitable for mass production.

The light guide rod 30, which is vibrated, is cantilevered. Thus, the use of a relatively short light guide rod 30 enables reduction of the dimensions of the microplate reader 1.

Figure 7A:
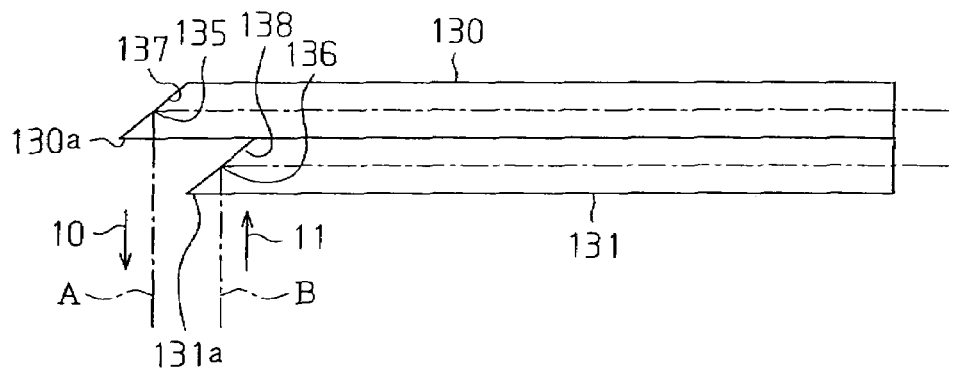
FIG. 7A is a side view showing a light guide rod included with a microplate reader according to a second embodiment of the present invention.
Figure 7B:
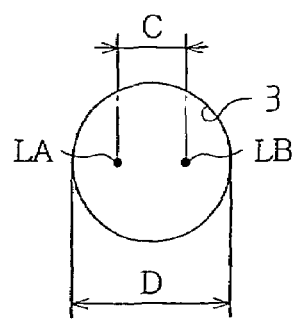
FIG. 7B is a diagram showing the distance between a light emitting portion and a light receiving portion in FIG. 7A and the dimensions of a measurement area.

A microplate reader 1 according to a second embodiment of the present invention will now be described with reference to FIGS. 7A and 7B.

The microplate reader 1 of the second embodiment includes two glass light guide rods 130 and 131. The light guide rod 130 is used for excitation light. The light guide rod 131 is used for return light. A light emitting portion 135 is defined by part of a reflection surface 137, which is formed on a distal end 130a of the light guide rod 130. A light receiving portion 136 is defined by part of a reflection surface 138, which is formed on a distal end 131a of the light guide rod 131.

The distance between the light emitting portion 135 and the light receiving portion 136 is equal to or less than the dimension of the top surface of each test sample 4. As shown in FIG. 7B, the distance C between a vertical line LA intersecting with the light emitting portion 135 and a vertical line LB intersecting with the light receiving portion 136 is less than the diameter D of the well 3, that is, the dimension of the top surface of each test sample 4. In the second embodiment, each of the light guide rods 130 and 131 is formed by an optical fiber including a core and a cladding. The light guide rods 130 and 131 are adhered to each other by an adhesive.

In the same manner as the first embodiment, the second embodiment provides a compact and inexpensive microplate reader 1 having high detection sensitivity.

It should be apparent to those skilled in the art that the present invention may be embodied in many other specific forms without departing from the spirit or scope of the invention. Particularly, it should be understood that the present invention may be embodied in the following forms.

The return light may be light other than fluorescence. For example, the return light may be luminescence, reflected light, or scattered light.

An elongated rod, which vibrates, and has a distal end including a light source, which functions as the light emitting portion, and a photodetector, which functions as the light receiving portion, may be used instead of the glass light guide rod 30. In this case, an electric wiring connected to the light source and an electric wiring connected to the photodetector are arranged on the rod.

The light guide rods 30, 130, and 131 do not have to be formed by an optical fiber including a core and a cladding. For example, the light guide rods 30, 130, and 131 may be formed by hollow light guide rods. This enlarges the usable wavelength range of the excitation light.

In the above embodiments, the light guide rods 30, 130, and 131 do not have to be made of glass and may be made of resin. It is preferred that the resin be optically transparent for excitation light and return light.

In the above embodiments, the optical system 50, the electric configuration shown in FIG. 5, the supporting members 61 and 62, and the magnet coils 72 may be integrated into one module, with the module fixed to the movable table 21. This facilitates the assembly of the microplate reader 1. A microplate reader 1 having this structure is suitable for mass production.

The distal end 30a of the light guide rod 30 does not have to be vibrated. In this case, the scanner mechanically moves the light emitting portion 5 and the light receiving portion 6 in a two-dimensional manner to scan the test samples 4. Or, the scanner may finely move the light emitting portion 5 and the light receiving portion 6 while placing the light emitting portion 5 and the light receiving portion 6 at a position facing one of the test samples 4. The distal end 30a of the light guide rod 30 may be vibrated so that the range of vibration extends across the plurality of wells 3 to scan the test samples 4 in the wells 3.

The XY stage 20 may be eliminated from the X-drive table 23, and a table for moving the microplate 2 in the X direction may be used instead. In this case, the microplate 2 is moved in the X direction, and the light guide rod 30 is moved only in the Y direction.

The present examples and embodiments are to be considered as illustrative and not restrictive, and the invention is not to be limited to the details given herein, but may be modified within the scope and equivalence of the appended claims.

What is claimed is:

1. A light detection device for irradiating each of a plurality of test samples, respectively accommodated in a plurality of measurement areas, with excitation light, and detecting return light from each of the test samples, wherein each measurement area has a predetermined dimension, the light detection device comprising:
 a light emitting portion for irradiating each measurement area with the excitation light;
 a light receiving portion for receiving the return light, wherein the light receiving portion is spaced from the light emitting portion by a predetermined distance that is less than the predetermined dimension; and a scanner for moving the light emitting portion and the light receiving portion in a range including the plurality of measurement areas to scan the measurement areas.

2. The light detection device according to claim 1, further comprising:

a glass light guide rod including a reflection surface, with the light emitting portion and the light receiving portion each being defined by part of the reflection surface.

3. The light detection device according to claim 2, wherein the light emitting portion and the light receiving portion are located at the same position on the reflection surface.

4. The light detection device according to claim 1, further comprising:

two glass light guide rods, each including a reflection surface, with the light emitting portion and the light receiving portion being respectively defined by parts of the reflection surfaces of the two light guide rods.

5. The light detection device according to claim 2, further comprising:

a light source for generating the excitation light;

a photodetector for detecting the return light; and an optical system optically coupled to the light source and the photodetector, the optical system directing the excitation light to enter a basal end of the light guide rod and directing the return light passing through the light receiving portion and the basal end of the light guide rod to enter the photodetector.

6. The light detection device according to claim 5, wherein the optical system includes a wavelength division element for permitting passage of the excitation light and, from the return light emitted from the basal end of the light guide rod, reflecting only light having a wavelength that differs from that of the excitation light.

7. The light detection device according to claim 2, wherein:

the plurality of measurement areas are arranged in a one-dimensional or two-dimensional manner on a substrate; and the scanner holds the substrate in a fixed state and mechanically moves the light emitting portion and the light receiving portion in a one-dimensional or two-dimensional manner to scan the plurality of measurement areas.

8. The light detection device according to claim 6, wherein the scanner includes an XY stage for moving the light guide rod in a two-dimensional manner.

9. The light detection device according to claim 2, wherein the plurality of measurement areas are arranged along a single plane, and the light guide rod has a distal end, including the reflection surface, and a cantilevered basal end, the light detection device further comprising:

a vibration unit for vibrating the distal end of the light guide rod parallel to the single plane using electromagnetic force.

10. A light detection device for emitting excitation light beam to one of a plurality of test samples placed on a substrate, and detecting return light beam from the one of the test samples, wherein each test sample has a diameter, the light detection device comprising:

a set of a light emitting portion for irradiating one of the test samples with the excitation light beam and a light receiving portion for receiving the return light beam, wherein the light receiving portion is spaced from the light emitting portion by a predetermined distance that is less than the diameter of each test sample; and a scanner for moving said set of the light emitting portion and the light receiving portion within a stroke so as to traverse the test samples to scan the test samples.

11. The light detection device according to claim 10, further comprising:

a vibration unit for vibrating said set of the light emitting portion and the light receiving portion within a movable range that is substantially equal to or less than the diameter of a test sample while said set of the light emitting portion and the light receiving portion are faced to the test sample.

12. The light detection device according to claim 11, wherein the vibration unit vibrates said set of the light emitting portion and the light receiving portion in a plane parallel to the substrate.

13. The light detection device according to claim 11, wherein the vibration unit vibrates the light emitting portion and the light receiving portion in a plane parallel to the substrate with a vibration width that is substantially equal to or less than the diameter of each test sample.

14. The light detection device according to claim 11, wherein the vibration unit vibrates the light receiving portion in a plane parallel to the substrate within the movable range while the light emitting portion irradiates one of the test samples with the excitation light beam.

* * * * *